(12) United States Patent
Elder et al.

(10) Patent No.: US 6,384,274 B1
(45) Date of Patent: May 7, 2002

(54) SINGLE REACTOR PROCESS FOR PREPARING ACRYLIC ACID FROM PROPYLENE HAVING IMPROVED CAPACITY

(75) Inventors: James Edward Elder; Charles Michael Lonzetta; Timothy Allen Hale, all of Houston, TX (US); John Dempster Sornson, Moorestown, NJ (US); Peter David Klugherz, Huntingdon Valley, PA (US); Thomas Albert Kaminski; Donald Alan Ebert, both of Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/244,182

(22) Filed: Feb. 4, 1999

Related U.S. Application Data
(60) Provisional application No. 60/102,219, filed on Sep. 29, 1998.

(51) Int. Cl.[7] ............................................... C07C 51/16
(52) U.S. Cl. ....................... 562/532; 562/542; 562/545
(58) Field of Search ................................ 562/545, 542, 562/532

(56) References Cited

U.S. PATENT DOCUMENTS

| | | | |
|---|---|---|---|
| 3,566,961 A | 3/1971 | Lorenz et al. ............... 165/169 |
| 3,798,264 A | 3/1974 | Kubota et al. | |
| 3,865,555 A | 2/1975 | Elebracht et al. ......... 23/288 R |
| 3,871,445 A | 3/1975 | Wanka et al. | |
| 4,147,885 A | 4/1979 | Shimizu et al. ............. 562/535 |
| 4,203,906 A | 5/1980 | Takada et al. ........... 260/346.4 |
| 4,256,783 A | 3/1981 | Takada et al. ............... 422/197 |
| 4,317,926 A | 3/1982 | Sato et al. | |
| 4,365,087 A | 12/1982 | Kadowaki et al. .......... 562/534 |
| 4,873,368 A | 10/1989 | Kadowaki et al. .......... 562/532 |
| 5,144,091 A | 9/1992 | Martan et al. .............. 568/479 |
| 5,161,605 A | 11/1992 | Gutlbuber ....................... 165/1 |
| 5,198,578 A | 3/1993 | Etzkorn et al. ............. 562/532 |
| 5,218,146 A | 6/1993 | Takata et al. | |
| 5,264,625 A | 11/1993 | Hammon et al. ........... 562/532 |
| 5,315,037 A | 5/1994 | Sakamoto et al. | |
| 5,739,391 A | 4/1998 | Ruppel et al. .............. 562/532 |
| 5,821,390 A | 10/1998 | Ruppel et al. .............. 568/470 |
| 5,892,108 A | 4/1999 | Shiotani et al. | |

FOREIGN PATENT DOCUMENTS

| | | |
|---|---|---|
| EP | 0 293 224 A1 | 11/1988 |
| EP | 0 911 313 A1 | 4/1999 |
| GB | 2 001 257 | 1/1979 |
| GB | 2 063 861 | 6/1981 |
| WO | WO 97/36849 | 3/1997 |

OTHER PUBLICATIONS

"A New Oxidation Process for Acrylic Acid from Propylene"; S. Sakuyama, T. Ohara, N. Shimizu, and K Kubota; Chemtec (Jun. 1973); pp 350–355).

William Bauer, Jr., "Acrylic Acid And Derivatives", Kirk–Othmer "Encyclopedia of Chemical Technology", vol. 1, pp. 287–314.

*Primary Examiner*—Johann Richter
*Assistant Examiner*—Brian J. Davis
(74) *Attorney, Agent, or Firm*—Alan Holler

(57) ABSTRACT

This invention relates to an improved process for preparing acrylic acid from propylene using a single reactor utilizing an increased amount of propylene reactant thereby providing increased capacity and throughput.

36 Claims, 3 Drawing Sheets

SINGLE REACTOR PROCESS FOR PREPARING ACRYLIC ACID FROM PROPYLENE HAVING IMPROVED CAPACITY

This is a nonprovisional application of prior pending provisional application Ser. No. 60/102,219 filed Sep. 29, 1998.

This invention relates to an improved process for preparing acrylic acid from propylene using a single reactor. In particular, the invention relates to a single reactor process for preparing acrylic acid from propylene utilizing an increased concentration of propylene reactant thereby providing increased capacity and throughput.

The preparation of acrylic acid from propylene generally proceeds in a vapor phase two step catalytic oxidation reaction. In the first step propylene is oxidized in the presence of oxygen, diluent inert gasses, water vapor, and appropriate catalysts to produce acrolein according to equation (I):

$$C_3H_6 + O_2 \rightarrow C_2H_3CHO + H_2O + \text{heat} \qquad (I).$$

The acrolein is then oxidized, in a second step, in the presence of oxygen, diluent inert gasses, water vapor, and appropriate catalysts to form acrylic acid according to equation (II):

$$C_2H_3CHO + \tfrac{1}{2} O_2 \rightarrow C_2H_3COOH + \text{heat} \qquad (II).$$

The two stage vapor phase catalytic oxidation of propylene to acrylic acid is generally performed using either tandem reactors wherein a separate reactor is utilized for each step (e.g., see the description in U.S. Pat. No. 4,873,368) or by utilizing one reactor to perform both steps (e.g., see the description in U.S. Pat. No. 4,526,783).

The acrylic acid prepared using such a vapor phase catalytic oxidation reaction is present in a mixed product gas exiting the reactor. Generally, the mixed product gas is cooled and is contacted with an aqueous stream in an absorption tower, thereby providing an aqueous acrylic acid solution from which acrylic acid can be isolated and purified. The remainder of the product gasses, known as the absorber waste gas or absorber off-gas, is incinerated or undergoes waste treatment. Depending on the reactants feed gas composition, the absorber off-gas may contain inert gasses, $O_2$, water vapor, $CO$, $CO_2$, unreacted propylene, unreacted acrolein and/or acrylic acid.

It is known in the art to recycle at least a portion of the absorber off-gas back to the reactor(s) to provide inert diluent gas and steam to the reactant composition. The propylene in the reactant composition must be diluted because at high propylene concentrations the reaction may proceed too quickly and become difficult to control. Recycle of the absorber off-gas provides the necessary diluent gasses and steam to the reactor feed to assure a suitable propylene concentration. In addition, recycling the absorber off-gas serves to reduce waste water generated by the process by reducing the amount of steam that is fed to the process. Furthermore, small amounts of unreacted propylene and acrolein contained in the off-gas are given another chance to react and thereby improve the overall acrylic acid yield by optimizing conversions of propylene and acrolein.

When absorber off-gas recycle is not used, steam and nitrogen are used as the primary diluents. Steam is not consumed, but may alter the selectivity, conversion and/or catalytic activity in the oxidation reactions and is part of the mixed product gasses emerging from the reactor. When the mixed product gasses are introduced into the absorption column, the steam substantially condenses tat the bottom of the absorption column and is a small part of the gasses flowing through the absorber.

However, a problem arises with absorber off-gas recycle. In contrast to the situation wherein absorber off-gas recycle is not used, a load develops at the top of the absorber because of the increased volume of inert gas flowing through the absorber. When absorber off-gas recycle is utilized, the off-gas is predominantly an inert gas such as nitrogen. When mixed product gasses containing such inert gasses are introduced into the absorber they do not generally condense at the absorber bottom, but rather remain part of the product gasses flowing through the absorber. Consequently, the increased inert gas content in the mixed product gasses introduced into the absorber causes an increase in the velocity of the gas flowing through the absorber. This results in a load at the top of the absorber. As the gas velocity gets higher, an increasing amount of product acrylic acid will remain with the absorber off-gas and be either lost to waste or be recycled back to the reactor. When it is recycled back to the reactor it can cause a decrease in catalyst activity. Consequently, regardless of whether it is lost to waste or recycles back to the reactor, the net result is a drop in acrylic acid yield.

A further problem results from the need to dilute the propylene in the gas feed to a manageable concentration. The dilution may be effected by absorber off-gas recycle or by adding steam and other inert materials or both. Because the two step oxidation of propylene to acrylic acid is highly exothermic, as the propylene concentration gets higher the danger of a runaway combustion increases. Also, the reaction mixture could become flammable and explode if ignited. Consequently, the oxidation of propylene to acrylic acid is generally practiced in the art utilizing a propylene concentration in the reactant gas feed composition of between 4 and 7 volume percent of the total reactant feed composition (see for example col. 2, lines 42–46 of U.S. Pat. No. 4,873,368). Accordingly, to assure control of the oxidation, propylene is diluted with steam and/or inert gasses such as nitrogen and combined with oxygen to form the feed composition. As a result, there is an additional load on the compressor which limits the capacity of the system. Consequently, any increase in capacity would require a larger compressor to handle the larger load.

As a result of the extra load on the absorber and on the compressor there is a limit on the capacity of the system which heretofore could not be remedied except by installation of larger equipment.

A further problem exists when tandem reactors are utilized. In tandem reactors there exists a high volume interstage between the two reactors through which the acrolein produced in the first reactor passes to the second reactor. This results in a longer residence time, compared to a single reactor, of the acrolein product in the interstage which may lead to homogenous reactions of acrolein and/or formation of foulants. Foulants may be formed by, for example, corrosion and deposition processes. Such homogeneous reactions are generally not catalytic, but rather are free radical reactions of acrolein which produce carbon oxides such as carbon dioxide and carbon monoxide, as well as other products such as acetaldehyde. Consequently, because of the longer interstage residence time in a tandem reactor process, steps such as cooling, reaction quenching, and acrolein dilution must be taken to reduce such homogeneous reactions of acrolein. In addition, the equipment and piping of the interstage is susceptible to gas leaks.

U.S. Pat. Nos. 4,365,087 and 4,873,368 have dealt with the problem of increasing process productivity/capacity by raising the propylene concentration level. However, the processes in these references used a tandem reactor process whereby either the temperature of the feed was limited (<260° C.), the oxygen to propylene ratio (1.1–2.0:1, preferably lower than 1.8) was kept low, additional oxygen and inert gas was fed to the second stage reactor, and the reaction was quenched somewhat before introduction to the second stage ('087) or the oxygen to propylene ratio (1.17–1.66:1) was even lower, additional oxygen and inert gas was fed to the second stage reactor, and the reaction was quenched somewhat before introduction to the second stage. Accordingly, the basis of the technique relied on two mechanisms for controlling the reaction at higher propylene concentrations:

(1) tightly controlling the temperature before entry into the first stage reactor and/or the second stage reactor; and (2) limiting the amount of oxygen initially available to the first reactor for oxidation of propylene to acrolein and then adding more oxygen and diluent at the interstage before the second stage reactor so that the second reactor feed has a stoichiometrically sufficient amount of oxygen to allow suitable oxidation of acrolein to acrylic acid.

However, this technique is unavailable for a single reactor system because it is implausible to add further oxygen and inert gas and quench the reaction at the interstage because both reactions of equations (I) and (II) occur in each of the reactor tubes of the single reactor. U.S. Pat. Nos. 4,256,783 and 4,203,906 describe a single reactor system which is useful in a variety of catalytic vapor phase oxidation reactions including the preparation of acrolein and/or acrylic acid. However, the example relating to acrylic acid (see columns 9 and 10, Example 5 of the '783 patent) does not utilize a reactant feed having a higher propylene concentration.

The present inventors have now discovered that with the single reactor system described herein it is possible to provide feeds to the reactor which contain a higher concentration of propylene than previously thought. Such higher concentration feeds are accomplished without the need to utilize a lower oxygen:propylene feed ratio, quenching of the reaction between stages and the consequent addition of oxygen and inert gas to the second stage to assure proper stoichiometry. Consequently, less absorber off-gas is required for dilution so that loads on the absorber and compressor are lightened resulting in an increase in capacity without additional capital expenditure.

Furthermore, a process is provided wherein homogeneous reactions of acrolein, as well as other interstage reactions, and interstage gas leaks are substantially eliminated.

Accordingly, a novel process for preparing acrylic acid from propylene is described herein wherein the following advantages are provided:

(1) increased throughput/capacity is provided without additional capital expenditure;

(2) downstream debottlenecking is realized through producing an aqueous acrylic acid stream in the absorber having a higher concentration of acrylic acid because less water is condensed and less acrylic acid is lost overhead in the absorber;

(3) since there is less water condensed in the aqueous acrylic acid there is a reduction in the waste generated by the process;

(4) less system energy is required because of the reduced compressor load;

(5) there is a lower pressure drop in the reactor, due to increased feed composition, which offsets increased propylene partial pressure, thereby preventing lower acrylic acid selectivity resulting from higher propylene pressure; and (6) interstage problems are substantially eliminated.

In one aspect of the present invention, there is provided a process for the vapor phase oxidation of propylene to acrylic acid, comprising the steps of: (A) feeding a reactant composition comprising: (i) greater than 7 percent by volume propylene, (ii) oxygen, (iii) water vapor, and (iv) the remainder including a major amount of at least one inert gas, into a reactor; the reactor including a plurality of contact tubes, containing at least one catalyst, disposed in a shell, wherein the inside of the reactor shell is divided into at least first and second heat transfer zones through each of which a heat transfer medium passes and each contact tube comprises two or more reaction zones capable of effecting the preparation of acrylic acid from propylene, and (B) contacting the reactant composition with the two or more reaction zones to form a mixed product gas comprising acrylic acid.

In a second aspect of the present invention, there is provided a process for the vapor phase oxidation of propylene to acrylic acid, comprising the steps of: (A) feeding a reactant composition comprising: (i) propylene (ii) oxygen, (iii), water vapor and (iv) the remainder being a major amount of at least one inert gas and a minor amount of at least one inert gas suitable for use as a fuel, into a reactor; the reactor including a plurality of contact tubes, containing at least one catalyst, disposed in a shell, wherein the inside of the reactor shell is divided into first and second heat transfer zones through each of which a heat transfer medium passes, wherein each contact tube comprises two or more reaction zones capable of effecting the preparation of acrylic acid from propylene, and (B) contacting the reactant composition with the two or more reaction zones to form a mixed product gas comprising acrylic acid.

In a third aspect of the present invention, there is provided a process for the vapor phase oxidation of propylene to acrylic acid, comprising the steps of: (A) feeding a reactant composition comprising: (i) greater than 7 percent by volume propylene, (ii) oxygen, (iii) water vapor, and (iv) the remainder being a major amount of at least one inert gas, into a reactor; the reactor including a plurality of contact tubes, containing at least one catalyst, disposed in a shell, wherein the inside of the reactor shell is divided into first and second heat transfer zones through each of which a heat transfer medium passes cocurrent to the reactant composition flow, wherein each contact tube comprises reaction zones A and A' which contain one or more catalysts capable of catalyzing oxidation of propylene to acrolein, reaction zones B and B' which contain one or more catalysts capable of catalyzing oxidation of acrolein to acrylic acid and a reaction zone C, containing a high surface area material having heat transfer properties and no percent catalyst, disposed between reaction zones A' and B, wherein the reaction zones A and A' have a different catalytic activity for converting propylene to acrolein and reaction zones B and B' have a different catalytic activity for converting acrolein to acrylic acid, and (B) contacting the reactant composition with the two or more reaction zones to form a mixed product gas comprising acrylic acid.

In a fourth aspect of the present invention, there is provided a reactant feed composition for vapor phase oxidation of propylene to acrylic acid in a single reactor, including: (i) 7.01 to 11 percent by volume propylene, (ii) oxygen in an amount suitable to provide an oxygen to propylene ratio of 1.6 to 2.2:1.0, (iii) 2 to 12 percent by volume water vapor, and (iv) the remainder comprising a major amount of at least one inert gas and a minor amount of at least one inert gas fuel.

Figure 1:
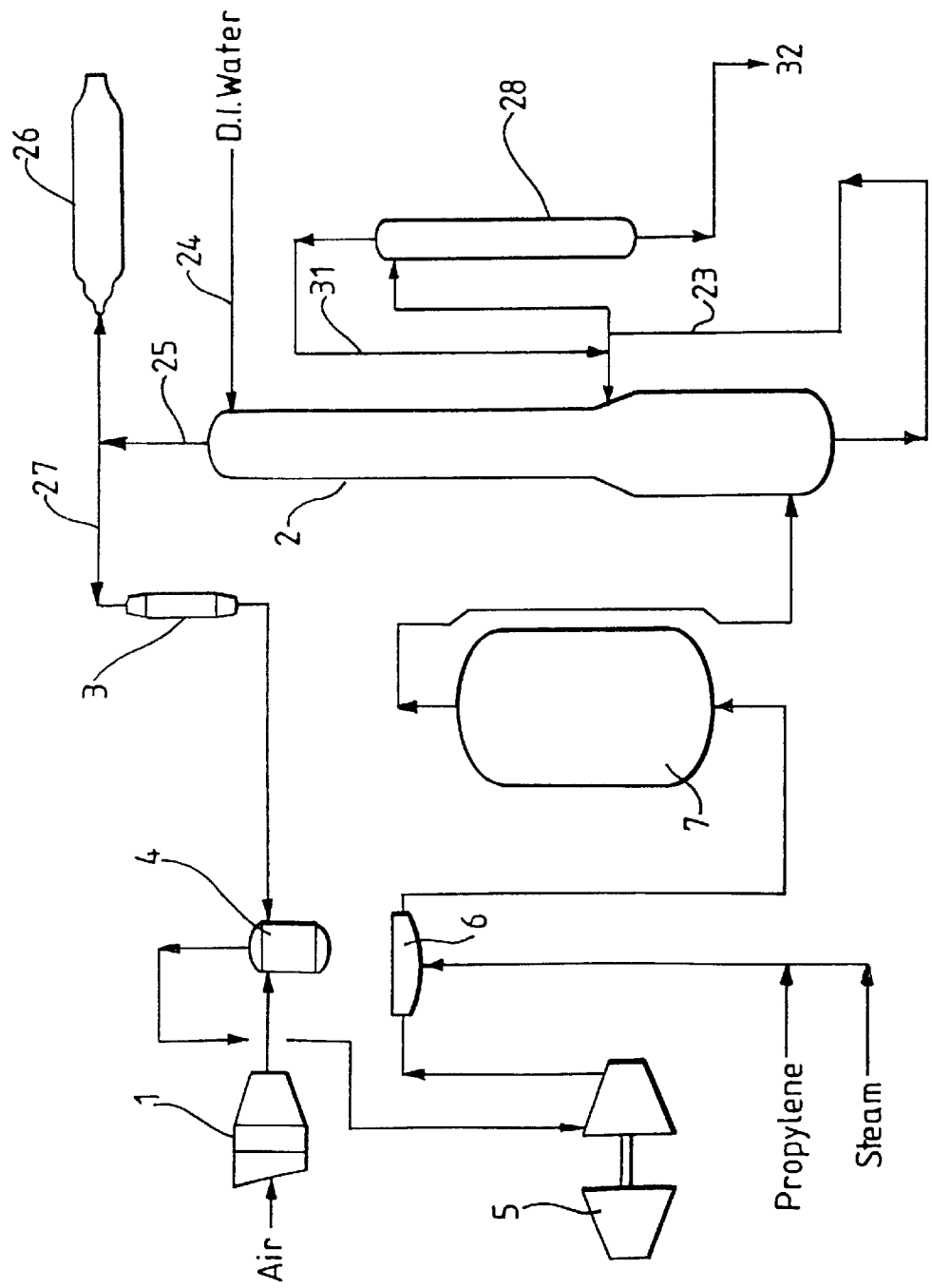
FIG. 1 depicts a flow chart showing one embodiment of the process of the present invention.

Throughout this specification and claims, unless otherwise indicated, references to percentages are by molar volume and all temperatures are in degree centigrade.

It is also to be understood that for purposes of this specification and claims that the range and ratio limits, recited herein, are combinable. For example, if ranges of 1–20 and 5–15 are recited for a particular parameter, it is understood that ranges of 1–15 or 5–20 are also contemplated.

Throughout this specification and claims the terms "water vapor" and "steam" are understood to be synonymous.

Also, the term "major amount" is understood to mean greater than 50 percent by volume of the total composition. The term "minor amount" is understood to mean less than 50 percent by volume of the total composition.

The term "cocurrent" as used herein is meant to indicate that the current of separate, distinct flowing materials is proceeding in substantially the same general direction, regardless of any alterations such as meandering, transverse, or radial flow.

The term "countercurrent" as used herein is meant to indicate that the current of separate, distinct flowing materials is proceeding in substantially the opposite general direction, regardless of any alterations such as meandering, transverse, or radial flow.

The term "inert" as used herein is meant to indicate that the particular material does not participate in, is unaffected by, and/or is otherwise inactive in the acrylic acid reaction system disclosed herein. Accordingly, a material such as propane is easily reacted or combusted in other systems, but in the reaction system of the present invention is considered inert. The term "catalyst" as used herein refers to pure catalysts, or pure catalyst provided on a support, by coating, impregnating etc., such pure catalyst on a support material. Accordingly, the terminology 100 percent catalyst refers not only to a material which is pure catalyst, but to 100 percent of a material which includes catalyst on a support material and/or impurities when purchased. That is, 100 percent catalyst refers to 100 percent of the catalyst as purchased, whether it be as neat chemical or with a support material.

The conversion % of propylene=(# moles propylene converted/# of moles propylene employed)×100.

The selectivity % of acrylic acid=(# of moles of acrylic acid produced/# of moles propylene reacted)×100.

The yield of acrylic acid=(# of moles acrylic acid produced/# of moles propylene employed)×100.

The yield of acrolein=(# of moles acrolein produced/# of moles propylene employed)×100.

As recited above, the process for preparing acrylic acid from propylene includes feeding a reactant composition into a reactor. The reactant composition includes propylene, oxygen, water vapor, and inert gas.

The propylene used may be from any source and may be any grade suitable for an acrylic acid producing vapor phase oxidation reaction. Suitable grades include, but are not limited to, polymer grade (generally greater than or equal to 99% propylene), chemical grade (generally greater than or equal to 94% propylene), and refinery grade (generally greater than or equal to 60% propylene). In a preferred embodiment, the propylene is chemical grade propylene. Use of chemical grade propylene has the added advantage of providing combustible materials such as propane which are present as impurities. The propane provides more inert gas to the system, but more importantly provides fuel for the thermal/catalytic oxidation or incineration of that portion of the absorber off-gas which is not recycled. Accordingly, the propane impurity enters the thermal/catalytic oxidizer or incinerator with the absorber off-gas and reduces the additional fuel required to burn the off-gas. Generally, chemical grade propylene contains up to 6 percent combustible impurities and refinery grade propylene contains up to 40 percent combustible impurities.

Propylene is generally present in the reactant composition at greater than 7 percent by volume of the reactant composition. In one embodiment, propylene is present at a range of from 7.01 to 11, preferably, 7.01 to 9 percent by volume of the reactant composition.

The oxygen in the reaction composition may be provided by any material containing an amount of oxygen sufficient to maintain the oxidation reactions in equations (I) and (II) above. Suitable examples include, without limitation, air, oxygen-enriched air, pure oxygen, and mixtures of pure oxygen and at least one inert gas or mixtures thereof. The preferred source of oxygen is air. Typically oxygen is present in the reactant composition in an amount suitable to meet the stoichiometric needs of the reaction. Generally, an amount of oxygen which will provide an oxygen/propylene ratio in the reactant composition of 1.6 to 2.2:1.0, preferably 1.6 to 2.0:1.0, is provided.

The water vapor in the reaction composition is generally present at a range from 2 to 12, preferably 5 to 11 percent by volume of the reactant composition. The water vapor may be provided by absorber off-gas recycle, or be otherwise generated and provided to the reactant composition or may be provided by both absorber off-gas recycle and generation.

The inert gas used in the reaction composition may be any gaseous material or mixtures of gaseous materials which is inert to the oxidation reactions depicted in equations (I) and (II) above. Typical examples include, but are not limited to, nitrogen, carbon dioxide, helium, argon, propane and carbon monoxide, or mixtures thereof. The preferred inert gas is nitrogen or a mixture of nitrogen with at least one other inert gas. The inert gas generally constitutes a major amount of the remainder of the reactant composition which is not propylene, oxygen, or water vapor. Generally, the inert gas is 50 to 99.9, preferably 60 to 99.9 volume percent of the remainder of the reactant composition.

As recited above, the reaction composition may optionally include at least one inert gas which is suitable for use as fuel for thermal oxidation/incineration of waste absorber off-gas. Such inert gas fuel may be provided as part of the impurities in the propylene feed, as part of the absorber off-gas, or as the neat chemical. Suitable examples include, but are not limited to, propane, ethane, methane, butane, pentane or mixtures of one or more of the above. The preferred inert gas fuel is propane. Generally, such inert gas fuel is present in a minor amount in the remainder of the reactant composition which does not include propylene, oxygen and water vapor. Generally, the inert gas fuel is 0.001 to 49.9, preferably 0.1 to 20 volume percent of the remainder of the reactant composition.

In a preferred embodiment, the water vapor and inert gas and optionally at least a portion of the inert gas fuel, of the reaction composition, are provided by recycle of the absorber off-gas to the reactor. Generally, an amount of absorber off-gas is recycled which is suitable to provide the appropriate amounts of water vapor and inert gas. However, it is understood by those skilled in the art that the absorber off-gas may not provide all of the requirements of water vapor and/or inert gas of the system and additional amounts may be added from other sources. The water vapor and inert gas from the absorber off-gas are combined with oxygen and propylene as shown in FIG. 1. Air is heated in inlet air heater 1 and is combined with recycle gas from the top of absorber 2 which has been reheated in the absorber off-gas reheater 3 in the suction 4 of the compressor 5. (The gasses are heated before mixing and feeding to the compressor to prevent fogging and/or condensation which might damage the compressor.) This mixture is pumped to the feed gas mixer 6 by the compressor 5 where the air and absorber off-gas mixture is combined with propylene and any additional steam required. The reactant composition is then fed to the reactor 7 at reactor inlet 29 into the contact tubes 9. The product gasses emerge from outlet 30.

Figure 2:
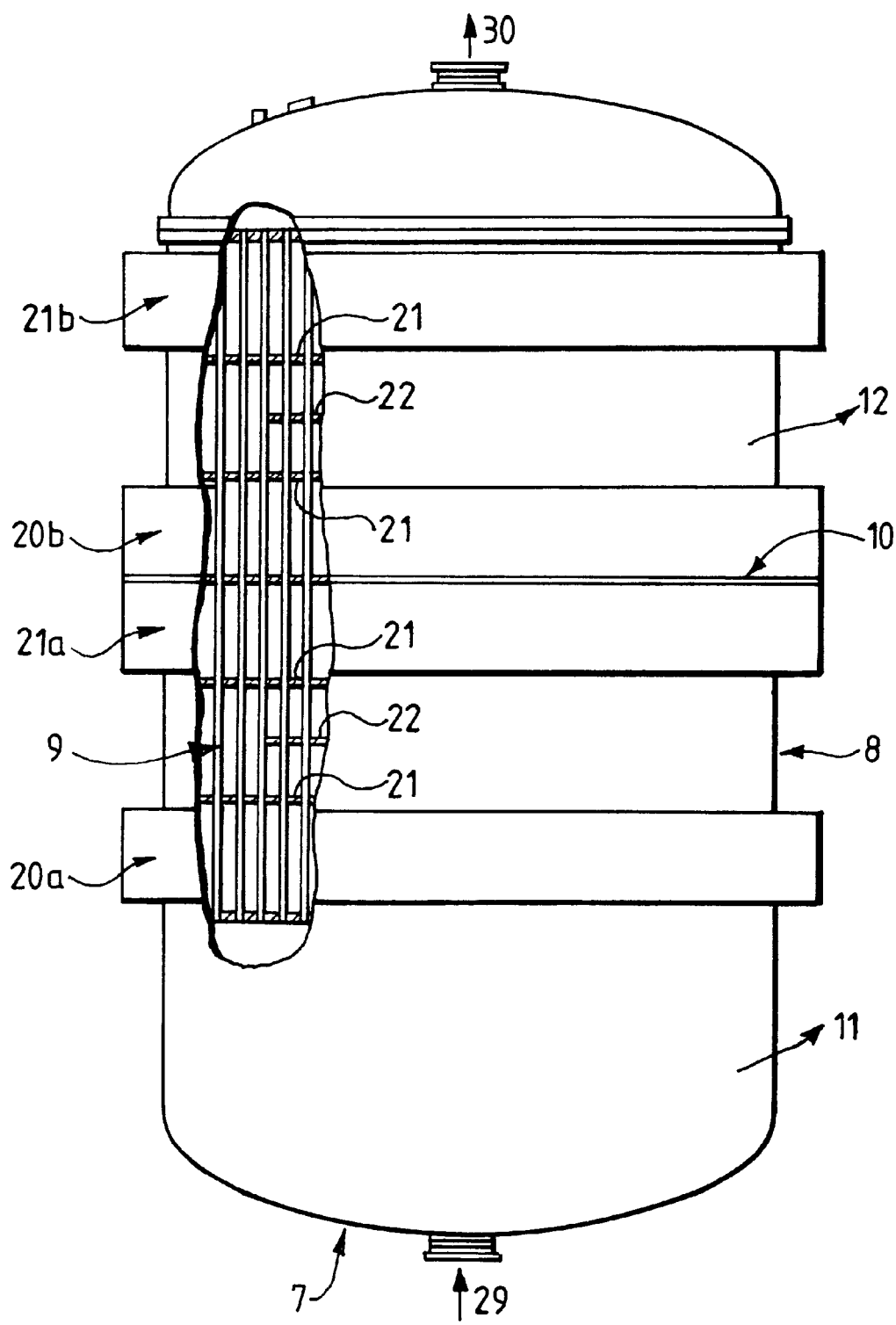
FIG. 2 depicts one embodiment of a reactor useful in the process of the present invention.

The reactor 7 is a shell and multiple contact tube heat exchange reactor. As depicted in FIG. 2, the reactor 7 includes a plurality of catalytic contact tubes 9 disposed in a shell 8 and passed through a perforated tube sheet 10 which divides the inside of the reactor shell into first heat transfer zone 11 and a second heat transfer zone 12 through each of which a heat transfer medium passes. The contact tubes 9 run longitudinally from the top portion to the bottom portion of the reactor 7 through the perforated tubesheet 10. It is understood that the reactor 7 may contain one or more perforated tubesheets which divide the reactor into two or more heat transfer zones.

Each of the plurality of contact tubes 9 includes two or more reaction zones which individually or in combination are capable of effecting the preparation of acrylic acid from propylene. At least one of the reaction zones contains a catalyst mixture capable of effecting the preparation of acrylic acid from propylene. In one embodiment, each of the contact tubes 9 contains a reaction zone A containing catalyst at least capable of catalyzing oxidation of propylene to acrolein and a reaction zone B containing catalyst at least capable of catalyzing oxidation of acrolein to acrylic acid. The reaction zones A and B may overlap or be intertwined or be disposed within the contact tubes 9 sequentially so that the reactants contact reaction zone A first and then reaction zone B.

In an alternative embodiment, each of the plurality of contact tubes 9 include reaction zones A and A' which contain one or more catalysts at least capable of catalyzing oxidation of propylene to acrolein and reaction zones B and B' which contain one or more catalysts at least capable of catalyzing oxidation of acrolein to acrylic acid. In one embodiment, reaction zones A and A' have a different catalytic activity for converting propylene into acrolein and/or reaction zones B and B' have a different activity for converting acrolein to acrylic acid.

In another embodiment, the two previous embodiments may be combined so that each contact tube 9 may have reaction zones A, A' and B; A, A', and B'; A, B, and B'; or A', B, and B'.

In a further embodiment, a reaction zone C containing 0 percent by weight catalyst is disposed between A type reaction zones (e.g., A or A' etc.) and B type reaction zones (e.g., B or B' etc.) in each contact tube 9. Generally, zone C is less than 10 percent of the total length of the contact tube. For instance in one embodiment zone C is 350 to 850, preferably 380 to 650 mm long. In a preferred embodiment, the reaction zone C is packed with a high surface area material with a heat transfer enhancing shape which is inert to and stable in the reaction system. Suitable examples include, alumina, alundum, mullite, carborundum, steel including stainless steel, copper, aluminum and ceramics. Furthermore, as stated above the material should be in a form in which its outer surface area is large including, without limitation, small spheres, cylinders, rings, small pieces, filament, meshes and ribbons.

Because of the short length of the reaction zone C, the reaction gasses have a short residence time in this zone of the contact tubes. As a result of this short residence time, the problems recited above which are inherent in a tandem reactor system do not occur in the process of the present invention. This is because gas wall molecular collisions occurring in zone C are enhanced by high surface area packing materials. Such molecular collisions tend to reduce the free radical homogenous reactions of acrolein by dissipating the kinetic energy of the system and therefore reduce free radical formation.

Figure 3:
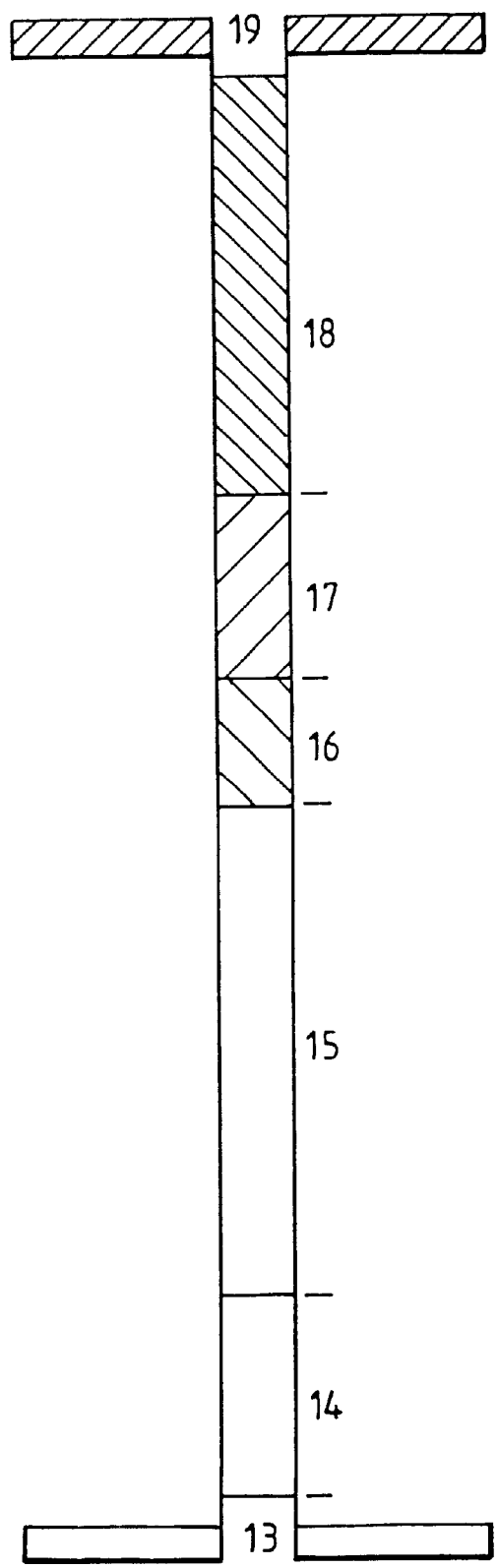
FIG. 3 depicts one embodiment of a catalytic contact tube of a reactor useful in the process of the present invention.

A preferred embodiment of a catalytic contact tube 9 of the present invention is shown in FIG. 3. The reaction gasses flow into reaction zone A at the bottom of the reactor. The first layer 13 in the bottom of contact tube 9 is a diluent material which is primarily ceramic balls or cylinders. Suitable ceramic materials as well as other type materials include, without limitation, one or more of the following: silicon dioxide, silicon carbide, silicon nitride, silicon boride, silicon boronitride, aluminum oxide (alumina), aluminosilicate (mullite), alundum, aluminoborosilicate, carborundum, carbon-fiber, refractory fiber, zirconium oxide, yttrium oxide, calcium oxide, magnesium oxide, magnesium oxide-aluminosilicate (cordite), and clay based materials. Suitable diluent materials are available, for instance, from Norton Chemical Process Products Corp., of Akron, Ohio as the Denstone® line of catalyst supports. As it passes the diluent material the reactant composition is preheated to near the temperature of the heat transfer medium before it enters reaction zone A 14. Reaction zone A 14 is a mixture of a catalyst capable of catalyzing the oxidation of propylene to acrolein and a diluent material. The mixture of catalyst and diluent material is less active than pure catalyst, thus making the reaction cooler and easier to control at the high initial propylene concentration. Determination of the amount of dilution of the catalyst is within the skill of those skilled in the art and generally is dependent on, for example, the particular catalyst utilized as well as the age of the catalyst and the operating conditions of the process. As the gas flows up the tube, the temperature increases as the reaction rate increases, then cools down as the propylene concentration decreases.

From reaction zone A 14 the reaction gasses flow into reaction zone A' 15 which has a higher catalytic activity than zone A 14. As a result, the reaction rate increases again and then decreases with declining propylene concentration. Zone A' 15 is longer than zone A 14, generally at least 50% longer, because more exposure to the higher activity catalyst is needed to convert substantially all of the propylene to acrolein which is being generated in situ in reaction zones A 14 and A' 15 along with some acrylic acid. Preferably, the ratio of the length of A'/A is 1.0:1 to 3.0:1, more preferably 1.5:1 to 2.5:1.

After traversing reaction zones A 14 and A' 15 the reaction gasses enter reaction zone C 16 which contains no catalyst but rather is packed with stainless steel Raschig rings or other suitable heat transfer material which have good heat transfer properties and increase the surface area of zone C. Reaction zone C 16 begins in the first heat transfer zone 11 and extends past the perforated tubesheet 10 into the second heat transfer zone 12. Reaction zone C 16 provides a short time for cooling the reaction gas to help control the oxidation reactions.

After passing reaction zone C 16 the reaction gasses enter reaction zone B 17. Reaction zone B 17 is a mixture of a catalyst capable of catalyzing the oxidation of acrolein to acrylic acid and a diluent material. As described for reaction zone A 14, the mixture of catalyst and diluent material is less active than pure catalyst, thus making the reaction cooler and easier to control at the high initial acrolein concentration generated in situ in zones A 14 and A' 15. Also, as described above, determination of the amount of dilution of the catalyst is within the skill of those skilled in the art and generally is dependent on, for example, the particular catalyst utilized as well as the age of the catalyst and the operating conditions of the process. As the gas flows up the tube the temperature increases as the reaction rate increases, then cools down as the acrolein concentration decreases.

From reaction zone B 17 the reaction gasses flow into reaction zone B' 18 which has a higher catalytic activity than zone B 17. As a result, the reaction rate increases again and then decreases with declining acrolein concentration. Zone B' 18 is longer than zone B 17, generally at least 50% longer, because more exposure to the higher activity catalyst is needed to maximize conversion of the acrolein to acrylic acid. Preferably, the ratio of the length of B/B is 1.0:1 to 3.0:1, more preferably 1.5:1 to 2.5:1.

The mixed product gas containing acrylic acid then flows out of the contact tubes 9 of the reactor 7 through a layer of inert material which is larger than the catalyst. The inert material holds catalyst within the contact tubes 9. Normal gas flows will not blow catalyst out of the tubes, but abnormal conditions might result in high gas velocities that could.

In one embodiment, the reactor 7 contains greater than 15,000 contact tubes 9. In a preferred embodiment, the reactor 7 contains greater than 25,000 contact tubes 9. The contact tubes 9 utilized are those generally known and used in the art. The contact tubes 9 may be arranged in any suitable arrangement known in the art. Such suitable arrangements are described and disclosed in, for instance, U.S. Pat. Nos. 4,256,783; 5,151,605; and DE 2,201,528.

Any catalysts suitable for the vapor phase catalytic oxidation of propylene to acrolein and acrolein to acrylic acid may be used in the process of the present invention. Such catalysts are known in the art and are described in, for instance U.S. Pat. Nos. 3,775,474; 3,893,951; 3,954,855; 4,075,127; 4,365,087; 4,873,368; 5,144,091; 5,177,260; 5,198,578; 5,264,625; 5,739,391; 5,739,392; WIPO Patent App. No. WO 97/36849; and Canadian Patent App. No. 2,114,681.

As recited above, the reactor 7 is divided into a first heat transfer zone 11 and a second heat transfer zone 12 by a perforated tubesheet 10 through which the contact tubes 9 pass. The first heat transfer zone 11 generally corresponds to that portion of the reactor 7 where the oxidation of propylene to acrolein predominantly occurs in the contact tubes 9. In a like manner, the second heat transfer zone 12, corresponds to that portion of the reactor 7 where oxidation of acrolein to acrylic acid predominantly occurs in the contact tubes 9. It is also recognized that some oxidation to acrylic acid may occur in reaction zones A and A' and oxidation of propylene to acrolein may occur in reaction zones B and B'. Accordingly, the contact tubes 9 are arranged so that the appropriate reaction zones are positioned in the appropriate heat transfer zone.

Each heat transfer zone has circulating within it a heat transfer medium which is used to maintain an effective catalyst temperature profile and therefore reaction temperature. Maintaining a desired catalyst temperature profile is required for maintaining the optimum acrylic acid yield and for optimizing catalyst life. If the reaction temperature is too high, more carbon dioxide and carbon monoxide are formed thereby resulting in lower yields. Furthermore, the catalyst will age quicker under excessive reaction temperatures. Of course, if the temperature gets high enough an uncontrolled runaway reaction may occur. If not controlled, such a reaction could lead to catalyst destruction and/or explosive conditions. If the reaction temperature is too low, less propylene will be converted to acrolein and acrolein to acrylic acid so that yields will be lower. If the reaction temperature is excessively low, propylene and/or acrolein may travel downstream leading to serious consequences.

The heat transfer medium circulates within each heat transfer zone thereby transferring heat from those outer portions of the contact tubes it contacts in the particular zone. The first heat transfer zone 11 is maintained at a temperature of 250 to 450, preferably 280 to 380° C.; and the second heat transfer zone 12 is maintained at a temperature of 220 to 450, preferably 240 to 360° C.

The peak catalyst temperatures are 20 to 70° C. above the heat transfer medium temperature and are very sensitive to changes in the heat transfer medium temperature. Generally, increasing the heat transfer medium temperature by 1° C. will increase the peak catalyst temperature by 2–3° C. As is known in the art the catalyst will lose activity as it grows older. To compensate, reaction temperature must be increased to maintain production of acrolein and acrylic acid at desired levels.

The heat transfer medium may circulate in any manner deemed suitable for the particular reactor system utilized. In one embodiment, the heat transfer medium circulates within the reactor cocurrent with the flow of the reactant gasses through the reactor. It is understood that the cocurrent flow may proceed top to bottom, bottom to top or side to side in the reactor 7. In an alternative embodiment, the heat transfer medium circulates within the reactor countercurrent with the flow of the reactant gasses through the reactor. In a preferred embodiment, the heat transfer medium circulates within the reactor both cocurrent with the flow of the reactant gasses and transverse both away from and towards the center of the reactor in a meandering flow. In a further preferred embodiment, a bypass flow of the heat transfer medium is provided. U.S. Pat. Nos. 4,256,783; 5,151,605; 5,739,391; and DE 2,201,528, describe and disclose contact tube and baffle arrangements in contact tube fixed bed shell reactors which provide for cocurrent, countercurrent, transverse and bypass flows of the heat transfer medium, such references being incorporated herein by reference for their teaching of heat transfer medium flow and reactor arrangements to accomplish the same. Furthermore, it is understood that the baffles may be arranged so as to have equal spacing between baffles or variable spacing between baffles.

The heat transfer medium may be any heat transfer medium suitable for use under the temperature conditions of the present invention. Generally the heat transfer medium is a salt melt, preferably a salt melt of 40 to 80, preferably 50 to 70 percent by weight potassium nitrate and 60 to 20, preferably 50 to 30 percent by weight sodium nitrite. In an alternative embodiment, the salt melt may include sodium nitrate as a substitute for sodium nitrite or potassium nitrate or as an additional component of the salt melt. The sodium nitrate is generally present at up to 20, preferably up to 10 percent by weight of the total salt composition. Other examples of heat transfer mediums include heat transfer oils, both oleaginous and synthetic, heat transfer fluids such as phenyl ethers and polyphenyls, and low melting metals such as sodium, tin, mercury, as well as low melting alloys of various metals.

In one embodiment, the heat transfer medium circulates within the reactor in at least two distinct heat transfer medium circuits. Preferably, at least one circuit is in each heat transfer zone. The heat transfer circuit is described as follows. The heat transfer medium enters the reactor shell at a plurality of points. In a preferred embodiment, the heat transfer medium flows into a channel 20a and 20b which completely circles the reactor 7. The heat transfer medium then flows from the channel 20a and 20b into the reactor 7 through windows in the shell of the reactor. Accordingly, the heat transfer medium flows into the reactor 7 around the reactor's entire perimeter. The heat transfer medium flows around the contact tubes and is forced into the center of the reactor by a doughnut baffle 21 which is a steel plate with a large hole in the center. The heat transfer medium flows through the hole and is forced back toward the perimeter of the reactor by a disk baffle 22 which is a large round plate which stops short of the reactor shell. The heat transfer medium flows through a series of the doughnut and disk baffles establishing a cocurrent/transverse flow of the heat transfer medium with the reactant gasses flow. After flowing through the baffles the heat transfer medium exits through windows through exit channels 21a and 21b, similar to the entry channel, back to heat transfer medium pumps for recirculation.

In an alternative embodiment, the heat transfer circuit contains a cooling circuit whereby a portion of the heat transfer medium of each heat transfer medium circuit is circulated to the outside of the reactor for cooling and then returned to the heat transfer medium circuit. In a further preferred embodiment, the heat transfer medium circulates within the reactor in at least two distinct heat transfer medium circuits at least one of which is a bypass circuit where at least a portion of the heat transfer medium circulates in a manner so as to bypass contact with at least a portion of the contact tubes 9. In an alternative preferred embodiment, the at least two distinct heat transfer medium circuits include two distinct heat transfer medium circuits as well as both a cooling circuit and a bypass circuit.

The process of the present invention optionally includes a step (C) contacting the mixed product gasses with an aqueous stream in an absorption tower 2 to obtain an aqueous acrylic acid solution. Generally, hot mixed product gasses exit the reactor and flow into the bottom section of the absorber wherein it is quenched by contact with a re-circulating absorber bottoms stream 23. A portion of the product acrylic acid is absorbed here while most of the remainder is absorbed in the upper section where the gas is contacted with an aqueous stream 24 fed into the top of the absorber. Any acrylic acid remaining in the absorber off-gas stream is sent to the incinerator 26 or recycled 27 to the reactor. Some of the reaction by-products, including acetic acid, formaldehyde, maleic acid and other organics, are absorbed along with the acrylic acid. Unreacted propylene, most of the unreacted acrolein, inert fuel gas such as propane, $CO_2$, $O_2$, CO, and $N_2$ are not absorbed and leave the absorber 2 as the absorber off-gas. Also part of the absorber off-gas is acrylic acid as well as other byproducts of the reaction which have not been absorbed. The absorber off-gas is sent to the thermal/catalytic oxidizer or incinerator or are recycled to the reactor as described above.

The aqueous stream 24 may be an essentially pure water stream, e.g., deionized water, a recycled aqueous wastewater stream or a mixture thereof. Typically, if a waste water stream is utilized the stream will contain a major amount of water and minor amounts of acrylic acid, acetic acid, distillation solvent(s), or mixtures of one or more thereof. In one embodiment, the recycled wastewater stream contains less than 3.0, preferably 0.001 to 2.5, more preferably 0.001 to 1.5 percent by weight acetic acid.

In a further embodiment, the aqueous stream 24 includes a polymerization inhibitor. The polymerization inhibitor may include a water soluble or alcohol soluble polymerization inhibitor. Suitable examples include but are not limited to, hydroquinone; 4-methoxyphenol; 4-ethoxyphenol; 4-propoxyphenol; 4-butoxyphenol; 4-heptoxyphenol; hydroquinone monobenzylether; 1.2-dihydroxybenzene; 2-methoxyphenol; 2,5-dichlorhydroquinone; 2,5-di-tertbutylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol; monobutylether; 4-ethylaminophenol; 2,3-dihydroxyacetophenone; pyrogallol; 1,2-dimethylether; 2-methylthiophenol; tbutyl catechol; di-tert-butylnitroxide; di-tert-amylnitroxide; 2,2,6,6-tetramethylpiperidinyloxy; 4-hydroxy-2,2,6,6-tetramethyl-piperidinyloxy; 4-oxo-2,2,6,6-tetramethyl-piperidinyloxy; 4-dimethylamino 2,2,6,6-tetramethyl-piperidinyloxy; 4-amino-2,2,6,6-tetramethyl-piperidinyloxy; 4-ethanoyloxy-2,2,6,6-tetramethylpiperidinyloxy; 2,2,5,5-tetramethyl-pyrrolidinyloxy; 3-amino-2,2,5,5-tetramethylpyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; copper compounds such as copper dimethyldithiocarbamate; copper diethyldithiocarbamate; copper salicylate; isomers thereof; mixtures of two or more thereof; or mixtures of one or more of the above with molecular oxygen. Preferably, the polymerization inhibitor is hydroquinone, 4-hydroxy-2,2,6,6-tetramethyl-piperidinyloxy, mixtures thereof; or mixtures of one or more of the above with molecular oxygen; more preferably the polymerization inhibitor is hydroquinone.

At least a portion of the absorber off-gas leaving the top of the absorber is recycled to the reactor as described above. The remaining portion is sent to a thermal oxidizer or incinerator wherein the organics in the stream are burned/oxidized for pollution prevention The process of the present invention optionally includes a step (D) stripping light ends from the aqueous acrylic acid solution emanating from the absorber 2 in a light ends stripper 28. Typically, the aqueous acrylic acid effluent from the absorber 2 is pumped to the light ends stripper 28. In the light ends stripper 28, light ends, including acrolein, are stripped out of the aqueous acrylic acid stream. The overhead stream from the light ends stripper is mostly water and acrolein which is condensed and recycled 31 to the absorber. This has the effect of concentrating the light ends in the absorber and eventually forcing them out in the absorber off-gas. The stripped aqueous acrylic acid solution from the bottom of the light ends stripper is introduced into a separations unit 32 wherein the acrylic acid is isolated and purified to provide the desired grade of acrylic acid product. Generally, the concentration of acrylic acid in the stripped aqueous acrylic acid solution is 55 to 85, preferably 60 to 80 percent by weight.

The polymerization inhibitor introduced into the absorber generally remains in the aqueous acrylic acid stream and inhibits polymerization of acrylic acid in the light ends stripping process. The following Examples are provided as an illustration of the present invention.

COMPARATIVE EXAMPLE 1

A feed composition containing 6.9% by volume chemical grade propylene, an amount of air and absorber off-gas sufficient to maintain an oxygen/propylene ratio of 1.9 and 8.9% by volume water vapor were fed to the contact tubes of a reactor as described by FIGS. 2 and 3. The reactants were introduced into the contact tubes which were packed with ACF-4 catalyst (zones A and A') and ACS-6 catalyst (zones B and B'), both available from Nippon Shokubai K.K. of Osaka, Japan, as described in FIG. 3. Zones A and B were diluted with inert Denstone 57® catalyst bed supports available from Norton Chemical Products Corp., of Akron, Ohio so that zone A was 66% catalyst and zone B was 87% catalyst where the ratio of the length of zones A/A' and B/B' are both ½. Zones A' and B' contained 100% of the ACF-4 and ACS-6 catalysts respectively. The acrylic acid formation reactions were carried out at a salt temperature maintained at 310 to 320° C. in Zone A and 300 to 310° C. in Zone B for a trial time of 12966 hours. The product gasses containing acrylic acid were introduced into an absorption tower to obtain an aqueous acrylic acid product solution. The aqueous acrylic acid solution was stripped of light ends in a light ends stripper to obtained an aqueous acrylic acid stream having an average concentration of 65.2 weight %.

EXAMPLE 1

This example was run according to the procedure of Comparative Example 1 except that the feed composition contained 7.6% by volume chemical grade propylene, an amount of air and absorber off-gas sufficient to maintain an oxygen/propylene ratio of 1.8 and 8.5% by volume water vapor and the Zone B salt temperature was maintained at 280 to 290° C. in Zone B. The Zone B salt temperature was different because the Zone B catalyst in the comparative example was a different age from that used in this example thereby requiring an adjustment in temperature to maintain the same catalytic activity. The trial time was 12545 hours. An aqueous acrylic acid stream having an average concentration of 69.5 weight % was obtained.

EXAMPLE 2

This example was run according to the procedure of Comparative Example 1 except that the feed composition contained 8.1% by volume chemical grade propylene, an amount of air and absorber off-gas sufficient to maintain an oxygen/propylene ratio of 1.8 and 7.6% by volume water vapor and the Zone B salt temperature was maintained at 280 to 290° C. in Zone B. The Zone B salt temperature was different because the Zone B catalyst in the comparative example was a different age than that used in this example thereby requiring an adjustment in temperature to maintain the same catalytic activity. The trial time was 23407 hours. An aqueous acrylic acid stream having an average concentration of 73.8 weight % was obtained.

The average overall propylene conversion, acrylic acid yield, and acrolein yield obtained for Comparative Example 1 and for Examples 1 and 2 remained substantially the same. The acrylic acid concentration in the aqueous stream emanating from the light ends stripper increased with increasing propylene percentage in the feed gasses. Accordingly, since the yield of acrylic acid remained substantially the same, the amount of acrylic acid produced per unit volume is increased. The ability to economically increase aqueous strength without excess acrylic acid losses in the absorber off-gas is illustrated by the general increase in acrylic acid concentration in the resulting aqueous stream. Generally, as the propylene partial pressure in the first stage of the reactor increases the acrylic acid yield decreases. This relationship is countered in the present invention by a decrease in reactor inlet pressure at higher propylene feed concentrations. The net result is that the overall AA yield is essentially constant as propylene concentrations are increased.

We claim:
1. A process for the vapor phase oxidation of propylene to acrylic acid, comprising the steps of:
(A) feeding a reactant composition comprising:
(i) greater than 7 percent by volume propylene,
(ii) oxygen,
(iii) water vapor, and
(iv) the remainder comprising a major amount of inert gas, into a reactor; the reactor including a plurality of contact tubes, containing at least one catalyst, disposed in a shell, wherein tic inside of the reactor shell is divided into at least first and second heat transfer zones through each of which a heat transfer medium passes and each contact tube comprises two or more reaction zones capable of effecting the preparation of acrylic acid from propylene, wherein the heat transfer zones are formed by at least one perforated tube sheet through which the catalytic contact tubes pass, and
(B) contacting tee reactant composition with the two or more reaction zones to form a mixed product gas comprising acrylic acid.
2. The process of claim 1, wherein the reactant composition contains 7.01 to 11 percent by volume propylene.
3. The process of claim 1, wherein in the reactant composition oxygen is present in an amount which provides an oxygen/propylene ratio of 1.6 to 2.0:1.0.
4. The process of claim 1, wherein the reactant composition contains 2 to 12 percent by volume water vapor.
5. The process of claim 1, wherein the two or more reaction zones include a reaction zone A containing catalyst at least capable of catalyzing oxidation of propylene to acrolein and a reaction zone B containing catalyst at least capable of catalyzing oxidation of acrolein to acrylic acid.
6. The process of claim 5, wherein the two or more reaction zones may overlap.
7. The process of claim 5, wherein the reaction zones A and B are disposed within the reactor tubes sequentially so that the reactants contact reaction zone A first and then reaction zone B.
8. The process of claim 1, wherein the two or more reaction zones include reaction zones A and A' which contain one or more catalysts at least capable of catalyzing oxidation of propylene to acrolein and reaction zones B and B' which contain one or more catalysts at least capable of catalyzing oxidation of acrolein to acrylic acid.
9. The process of claim 8, wherein the reaction zones A and A' have a different catalytic activity for converting propylene to acrolein.
10. The process of claim 9, wherein reaction zones B and B' have a different catalytic activity for converting acrolein to acrylic acid.

11. The process of claim 5, wherein the contact tube further comprises a reaction zone containing 0 percent catalyst disposed between the first and second reaction zones.

12. The process of claim 8, wherein the contact tube further comprises a reaction zone containing 0 percent catalyst disposed between reaction zones A' and B.

13. The process of claim 1, wherein the reactor contains greater than 15,000 contact tubes.

14. The process of claim 8, wherein the ratios of A'/A and B'/B are both 1.0:1 to 3.0:1.

15. The process of claim 1, wherein the first heat transfer zone is maintained at a temperature of 250 to 450° C.

16. The process of claim 1, wherein the second heat transfer zone is maintained at a temperature of 220 to 450° C.

17. The process of claim 1, wherein the heat transfer medium circulates within the reactor cocurrent with the flow of the reactants.

18. The process of claim 1, wherein the heat transfer medium circulates within the reactor countercurrent with the flow of the reactants.

19. The process of claim 1, wherein the heat transfer medium circulates within the reactor in at least two distinct heat transfer medium circuits.

20. The process of claim 1, wherein the heat transfer medium enters the reactor through the shell at a plurality of entry points.

21. The process of claim 17, wherein the heat transfer medium circulates within the reactor both cocurrent with the reactants and transverse both away from and towards the center of the reactor in a meandering flow.

22. The process of claim 18, wherein at least one of the heat transfer medium circuits contains a cooling circuit whereby a portion of the heat transfer medium of the heat transfer medium circuit is circulated to the outside of the reactor for cooling and then returned to at least one of the heat transfer medium circuits.

23. The process of claim 18, wherein the heat transfer medium circulates within the reactor in at least two distinct heat transfer medium circuits, at least one of which is a bypass circuit where at least a portion of the heat transfer medium circulates in a manner so as to bypass contact with at least a portion of the contact tubes.

24. The process of claim 1, further comprising step (C) contacting the mixed product gas with an aqueous stream in an absorption tower to obtain an aqueous acrylic acid solution.

25. The process of claim 24, wherein at least a portion of absorber off-gas produced during step (C) is combined with reactants to form the reactant composition.

26. A. The process of claim 25, wherein the portion of absorber off-gas provided is an amount suitable to maintain greater than 7 by volume propylene in the reactant composition.

27. The process of claim 24, wherein the aqueous stream comprises water and at least one polymerization inhibitor.

28. The process of claim 27, wherein the at least one polymerization inhibitor is selected from a water soluble or alcohol soluble polymerization inhibitor.

29. The process of claim 27, wherein the at least one polymerization inhibitor is utilized in combination with oxygen.

30. The process of claim 24, wherein the aqueous stream comprises less than 3.0 percent by weight acetic acid.

31. The process of claim 30, wherein at least a portion of the aqueous stream is a recycled waste water stream.

32. The process of claim 24, further comprising step (D) stripping light ends from the aqueous acrylic acid solution emanating from the absorber.

33. As process for the vapor; phase oxidation of propylene to acrylic acid, comprising the steps of:
(A) feeding a reactant composition comprising:
(i) propylene,
(ii) oxygen,
(iii) water vapor, and
(iv) with the remainder being a major amount of at least one inert gas and
a minor amount of at least one inert gas suitable for use as a fuel, into a reactor; the reactor including a plurality of contact tubes containing at least one catalyst disposed in a shell, wherein the inside of the reactor shell is divided into first and second heat transfer zones through each of which a heat transfer medium passes, wherein each contact tube comprises two or more reaction zones capable of effecting the preparation of acrylic acid from propylene, wherein the beta transfer zones axe formed by at least one perforated tube sheer through which the catalytic contact tubes pass, and
(B) contacting the reactant composition with the two or more reaction zones to form a mixed product gas comprising acrylic acid.

34. A process for the vapor phase oxidation of propylene to acrylic acid, comprising the steps of:
(A) feeding a reactant composition comprising:
(i) greater than 7 percent by volume propylene,
(ii) oxygen,
(iii) water vapor, and
(iv) the remainder being a major amount of at least one inert gas,
into a reactor; the reactor including a plurality of contact tubes containing at least one catalyst disposed in a shell, wherein the inside of the reactor shell is divided into first and second heat transfer zones through each of which a heat transfer medium passes cocurrent to the reactant composition flow, wherein each contact tube at least comprises reaction zones A and A' which contain one or more catalysts capable of catalyzing oxidation of propylene to acrolein, reaction zones B and B' which contain one or more catalysts capable of catalyzing oxidation of acrolein to acrylic acid and a reaction zone C, containing a high surface area material having heat transfer properties and 0 percent catalyst, disposed between reaction zones A' and B, wherein the reaction zones A and A' have a different catalytic activity for converting propylene to acrolein and reaction zones B and B' have a different catalytic activity for converting acrolein to acrylic acid, wherein the heat transfer zones are formed by at least one perforated tube sheet through which the catalytic contact tubes pass, and
(B) contacting the reactant composition with the two or more reaction zoned to form a mixed product gas comprising acrylic acid.

35. A reactant composition for vapor phase oxidation of propylene to acrylic acid in a single reactor, consisting of:
(i) 7.01 to 11 percent by volume propylene,
(ii) oxygen in an amount suitable to provide an oxygen to propylene ratio of 1.6 to 2.2:1.0,
(iii) 2 to 12 percent by volume water vapor, and
(iv) the remainder being an inert gas selected from the group consisting of nitrogen, helium, argon and mixtures thereof.

36. The reactant composition of claim 35, wherein the inert gas is nitrogen.

* * * * *